United States Patent [19]

Acklin et al.

[11] Patent Number: 4,847,374

[45] Date of Patent: Jul. 11, 1989

[54] PROCESS FOR THE MANUFACTURE OF N,N-(DIBENZOHEXATRIENYLENE)UREAS

[75] Inventors: Georg Acklin, Arlesheim; Ernst Aufderhaar, Kaiseraugst; Günter Kaupp, Witterswill; Bernhard Räz, Basel; Ulrich Vogel, Magden, all of Switzerland

[73] Assignee: Ciba-Geigy Corporation, Ardsley, N.Y.

[21] Appl. No.: 145,430

[22] Filed: Jan. 19, 1988

[30] Foreign Application Priority Data

Jan. 27, 1987 [CH] Switzerland .................. 276/87

[51] Int. Cl.$^4$ .................................. C07D 223/26
[52] U.S. Cl. .................................. 540/589; 540/592
[58] Field of Search .................................. 540/589, 592

[56] References Cited

U.S. PATENT DOCUMENTS 2,948,718  8/1960  Schindler .................. 260/239
4,436,660  3/1984  Aufderhaar et al. .......... 260/239 D

OTHER PUBLICATIONS

Durant et al., Chem. and Industry, (8/65), pp. 1428–1429.

Primary Examiner—David B. Springer
Attorney, Agent, or Firm—Irving M. Fishman; JoAnn Villamizar

[57] ABSTRACT

N,N-(dibenzohexatrienylene)urea medicaments can be manufactured in a smooth one-step reaction by reacting a corresponding N,N-(dibenzohexatrienylene)amine with cyanic acid.

12 Claims, No Drawings

PROCESS FOR THE MANUFACTURE OF N,N-(DIBENZOHEXATRIENYLENE)UREAS

The invention relates to a process for the manufacture of N,N-(dibenzohexatrienylene)ureas, especially 1,5-dibenz[b,f]azepine-5-carboxamide, characterised in that a corresponding N,N-(dibenzohexatrienylene)amine, especially 1,5-dibenz[b,f]azepine (iminostilbene), is reacted with cyanic acid.

1,5-Dibenz[b,f]azepine-5-carboxamide, known by the generic name carbamazepine as an active ingredient in medicaments, is, in accordacne with U.S. Pat. No. 2 948 718, usually manufactured by reacting iminostilbene with phosgene to form 1,5-dibenz[b,f]azepine-5-carboxylic acid chloride and by further reaction of the same with ammonia. In accordance with a more recent process according to DE-Al 2307174, iminostilbene is reacted with an acylisocyanate and the resulting 1,5-bidenz[b,f]azepine-5-(N-acyl)carboxamide is subjected to basic hydrolysis. The known processes have decided disadvantages. Two separate reaction steps must always be carried out, and in the first step of the process according to the US-PS the use of an equimolar amount of highly toxic phosgene is unavoidable.

The object of the invention was accordingly to address the hitherto unsolved problem of developing a manufacturing process that in one step results directly in 1,5-bidenz[1,5]azepine-5-carboxamide.

The proposed solution according to the invention is surprising in as much as it is known that when iminostilbene is reacted with alkylisocyanates it does not form corresponding 1,5-dibenz[b,f]azepine-5-(N-alkyl)carbozamides (DE-Al 2307174) and the reaction of N,N-diarylamines with sodium cyanate and trifluoroacetic acid in benzene could not be used in the case of N,N-(benzobutadienylene)-and N,N-(dibenzobutadienylene)-amines, such as indole and carbazole, respectively (Chem. and Ind. 1965, pages 1428–9).

The process for the manufacture of carbamazephine of the present invention comprises reacting iminostilbene (a) in an aliphatic carboxylic acid; an aliphatic carboxylic acid in the presence of a mineral acid; or an aliphatic ester in an aliphatic carboxylic acid, an aromatic or araliphatic hydrocarbon or a haloaliphatic solvent and in the presence of a mineral acid with cyanic acid; or (b) in an aliphatic carboxylic acid, an aliphatic ester of an aliphatic carboxylic acid, an aromatic or araliphatic hydrocarbon or a halo-aliphatic solvent with a salt of cyanic acid and an excess of a mineral acid.

The cyanic acid used in accordance with the invention to introduce the 5-carbamoyl group is usually produced by pyrolysis of cyanuric acid, by oxidation of formamide with oxygen with silver or copper contact or by treating a solution and/or suspension of one of its salts, preferably sodium or potassium cyanate, with an acid. Cyanic acid is not stable in free form. It enters into a large number of polymerisation and autocondensation reactions and in addition readily adds water, alcohols, amines and the like. Solutions thereof in suitable organic solvents are, however, adequately stable for the purpose of the invention.

The reaction according to the invention is therefore preferably carried out in organic solution, that is to say in an organic solvent or a mixture of organic solvents, cyanic acid preferably being blown into the reaction system in a gaseous state, advantageously with the aid of an acid by treating a solution and/or suspension of one of its salts, preferably sodium or potassium cyante.

Suitable organic solvents are those that do not react with isocyanic acid or that react with isocyanic acid only so slowly that the reaction according to the invention is not impaired by the formation of undesirable intermediates. The following, for example, are suitable: aromatic or araliphatic hydrocarbons such as benzene or toluene, haloaliphatic compounds such as 1,2-dichloroethane, aliphatic carboxylic acids and the aliphatic esters thereof, such as lower alkanecarboxylic acids, for example acetic acid, or lower alkanecarboxylic acid lower alkyl esters, for example ethyl acetate, and also aliphatic ethers such as diethyl ether, dioxan, tetrahydrofuran and the like, as well as mixtures of the same.

Since cyanic acid enters into undesirable secondary reactions with water, alcohols, amines and the like, the reaction according to the invention is advantageously carried out under essentially aprotic conditions, that is to say, in essentially water-, alcohol- and amine-free organic solution and with the exclusion of water vapour. These precautionary measures can be dispensed with completely, however, when working up the reaction mixture and isolating the addition product formed.

An amount of cyanic acid at least equimolar to the N,N-(dibenzohexatrienylene)amine used is necessary for the reaction according to the invention. To achieve a better reaction yield, however, advantageously from approximately 1.05 to approximately 2.5 times the molar amount, preferably from approximately 1.25 to approximately 2.25 times the molar amount, for example from approximately 1.3 to approximately double the molar amount, of cyanic acid is used, that is to say, an approximately 5 % to approximately 150 %, preferably an approximately 25 % to approximately 125 %, for example an approximately 30 % to approximately 100 %, excess of cyanic acid is used.

To free cyanic acid from one of its salts, which is an especially preferred embodiment of the invention, in general any protonic acid with an acidic strength sufficient to free cyanic acid from its salts is suitable. The following, for example, are suitable: mineral acids, for example hydrochloric acid or sulphuric acid, organic sulphonic acids such as $C_1$–$C_7$-alkanesulphonic acids or optionally halo- or $C_1$–$C_4$-alkyl-substituted benzenesulphonic acids, for example methane-, ethane-, benzene-, p-toluene- or p-bromobenzene-sulphonic acid, or organic carboxylic acids of which the acidic strength in the solvent used corresponds in practice at least to that of formic acid, such as 2-mono-, 2,2-di- or 2,2,2-tri-halo-$C_2$-$C_7$-alkanoic acids, for example trichloroacetic acid.

The reaction of the N,N-(dibenzohexatrienylene)amine component with cyanic acid is spontaneous and slightly exothermic. The parameters of the reaction are not critical. The reaction can be carried out, for example, in a temperature range of from approximately 0° C. to approximately 120° C. and homogeneously or, preferably, heterogeneously. The reaction is, however, accelerated, and the reaction speed increased, by heating gently and/or by the presence of an acidic medium. The reaction is therefore preferably carried out in a temperature range of from room temperature, that is to say approximately 20° C., to approximately 100° C., and in the presence of an acidic agent. Since th participation of the latter in the reaction is only catlytic, in principle catalytic amounts of acid are sufficient. In general, from approximately 0.01 to approximately 0.15, for example from approximately 0.04 to approximately 0.05, of an equivalent of acidic agent per mol of N,N-(dibenzohexatrienylene)amine is entirely adequate. Only when using polybasic acids of distinctly different acidity stages is it necessary to note in the case of heterogeneous reaction that acidic salts may be precipitated, blocking some of the acid used. When using sulphuric acid, for example, it is therefore necessary to use per mol of N,N-(dibenzohexatrienylene)amine up to 1.5 mol equivalents, for example from approximately 1.05 to approximately 1.4 mol equivalents, of sulphuric acid, corresponding to approximately 0.525 to approximately 0.7 mol, that is to say an approximately 5 % to approximately 40 % excess, if using the variant in which cyanic acid is freed from one of its salts and the reaction is carried out heterogeneously. Obviously, the catalytic acidic agent may alternatively be present or be added in the form of the corresponding N,N-(dibenzohexatrienylene)ammonium salt.

Suitable acidic agents are, for example, the protonic acids indicated above as being suitable for freeing cyanic acid, and also aliphatic carboxylic acids such as $C_1$-$C_7$-alkanoic acids, for example acetic acid, especially if these also act as solvents. If the variant in which cyanic acid is freed in situ from one of its salts is used, then it is generally advantageous to employ a small excess, that is an excess of from approximately 0.5 % to approximately 10 %, for example from approximately 1 % to approximately 5 %, of the acid used for freeing cyanic acid but if, for example, sulphuric acid is used, then, for the reasons mentioned, it is advantageous to employ an approximately 5 % to approximately 40 % excess, for example an approximately 32 % excess.

In a preferred embodiment that is added to a suspension of the N,N-(dibenzohexatrienylene)amine, especially iminostilbene, and of at least the equimolar amount, especially from approximately 1.7 5 to approximately 2.25 times the molar amount, for example approximately doubel the molar amount, of sodium cyanate in toluene, at from approximately 20° C. to aproximately 30° C. , for example at frm room temperature to approximately 25° C., per mol of sodium cyanate, from approximately 1.005 to approximately 1.5 mol, for example 1.02 mol, of trichloroacetic acid, that is to say an approximately 0.5 % to approximately 5 %, for example an approximately 2 %, excess of trichloroacetic acid, and the whole is heated, if necessary, to from approximately 40° C. to approximately 80° C., for example to approximately from 50° C. to 65° C.; or there is added to a suspension of hte N,N-(dibenzohexatrienylene)amine, especially iminostilbene, in acetic acid, from approximately 1.05 to approximately 1.40 mol equivalents of sulphuric acid, corresponding to from approximately 0.525 mol to approximately 0.7 mol, that is to say an approximately 5 % to approximately 40 % excess, of sulphuric acid, and there is then added an amount of sodium cyanate that is at least equimolar to the amount of N,N-(dibenzohexatrienylene)amine used, for example from approximately 1.25 to approximately 1.75 mol, for example approximately 1.6 mol, of sodium cyanate per mol of the amine, the operation being carried out, for example, at from approximately 10° C. to approximately 120° C.; or there is introduced into a suspension of sodium isocyanate in ethyl acetate approximately from 1.02 to 1.40 times the molar amount, for example approximately 1.05, that is to say from 1.04 to 1.06, times the molar amount of hydrogen chloride, that is a small excess, preferably an approximately 2 % to approximately 10 % excess, for example an approximately 5 % excess, that is to say an excess of from 4% to 6%, of hydrogen chloride and there is then added an amount of N,N-(dibenzohexatrienylene)-amine that is at most equimolar to the amount of sodium cyanate used, for example an approximately 5 % to approximately 50 % molar deficit, for example from approximately 0.6 to approximately 0.9 mol, for example approximately .075 mol, of iminostilbene per mol of sodium cyanate, the operation preferably being carried out at from approximately 0° C. to approximately 80° C., for example with heating to approximately from 40° C. to 70° C. after the addition of the amine component.

In another preferred embodiment, there is introduced into a suspension of the N,N-(dibenzohexatyrienylene)amine, especially iminostilbene, in acetioc acid, at least the equimolar amount, for example from approximately 1.25 to approximately 1.75 times the molar amount, preferably from approximately 1.4 to approximately 1.6 times the molar amount, that is to say a, for example, approximately 25% to approximately 75%, preferably approximately 40% to approximately 60%, excess of cyanic acid and the whole is heated, if necessary, to from approximately 25° C. to approximately 50° C.; or there is introduced into a suspension of the N,N-(dibenzohexatrienylene)amine, especially iminostilbene, in toluene, xylene, 1,2-dichloroethane or ethyl acetate, first of all from approximately 0.01 to approximately 0.15 times the molar amount, for example from 0.01 to approximately 0.12 times the molar amount, that is to say from approximately 1 to approximately 15 mol %, for example from approximately 1 to approximately 12 mol %, of hydrogen chloride and then at least the equimolar amount, for example from approximately 1.25 to approximately 1.75 times the molar amount, preferably from approximately 1.4 to approximately 1.6 times per molar amount, that is to say a, for example, approximately 25 % to approximately 75 %, preferably approximately 40 % to approximately 60 %, excess of cyanic acid, and the whole is then heated, if necessary, to from approximately 50° C. to approximately 125° C., for example to from approximately 75° C. to approximately 100° C. In a modification of this variant, there is introduced into a suspension of a mixture of the N,N-(dibenzohexatrienylene)amine and one of its acid addition salts, for example from approximately 0.8 to approximately 0.96, preferably from approximately 0.85 to approximately 0.95, molar proportions of iminostilbene and from approximately 0.04 to approximately 0.2, preferably from approximately 0.05 to 0.15, molar proportions of iminostilbene hydrochloride (total of molar proportions=1), at least the equimolar amount of cyanic acid, for example from approximately 1.25 to approximately 1.75 times the molar amount, preferably from approximately 1.4 to approximately 1.6 times the molar amount, that is to say a, for example, approximately 25% to approximately 75%, preferably approximately 40% to approximately 60%, excess of cyanic acid, and the whole is heated, if necessary, to from approximately 60° C. to approximately 100° C.

The invention is described in detail in the following Examples. Temperatures are given in degrees Celsius.

EXAMPLE 1

723 g of trichloroacetic acid are dissolved in 600 ml of toluene and, in the course of 1½ hours, this solution is added to a suspension of 407 g of iminostilbene and 290 g of sodium cyanate in 600 ml of toluene, the temperature being maintained at 25° C. by cooling.

The whole is then allowed to react for ½ hour at 25° C. and for 1 hour at 50° C. and 1300 ml of water are subsequently added slowly. The mixture is then cooled to 20° C. and the product is filtered off, washed with toluene and water and drived at 85°–90° C. in vacuo. Yield: 475 g of carbamazepine.

EXAMPLE 2

25 g of iminostilbene are suspended in 180 ml of acetic acid and 14 g of 96 % sulphuric acid are slowly added. 13.5 g of sodium cyanate are added in portions at 30° C. while stirring well.

The whole is stirred for 3 hours at 30° C., and the product is filtered off and washed with acetic acid and then with water. 29.5 g of carbamazepine are obtained after drying at 80° C. in vacuo.

EXAMPLE 3

68 g of sodium cyanate are suspended in 1000 ml of ethyl acetate and, while stirring at room temperature, 40 g of hydrogen chloride in gaseous form are introduced. After 4 hours, the sodium chloride that has formed is filtered off and 155 g of iminstilbene are added to the clear filtrate. The reaction mixture is maintained at 50° C. for from 4 to 5 hours, cooled to 0° C. and the product is filtered off, washed with a small amount of ethyl acetate and dried at 80° C. in vacuo to yield 177 g of carbamazepine.

EXAMPLE 4

17.4 g of iminostilbene and 2.3 g of iminostilbene hydrochloride are suspended in 250 ml of toluene. The suspension is heated to 80° C. and, in the course of 1½ hours, 6.5 g of monomeric cyanic acid are introduced in a stream of nitrogen and the whole is then heated for a further ½ hour at 100° C.

After cooling to 5° C., the product is filtered off, washed four times with cold toluene and dried in vacuo at 60° C. b 18.5 g of carbamazepine are obtained.

EXAMPLE 5

17.4 g of iminostilbene and 2.3 g of iminostilbene hydrochloride are suspended in 250 ml of xylene (isomeric mixture). At 20° C., 6.5 g of monomeric cyanic acid are introduced in a stream of nitrogen and the whole is then allowed to react for 4 hours at 30° C.

Subsequently, the whole is cooled to 0° C., and the product is filtered off, washed with xylene and dried in vacuo at 80° C. to yield 22.1 g of carbamazepine.

EXAMPLE 6

19.3 g of iminostilbene are suspeneded in 200 ml of 1,2-dichloroethane. At 25° C., first of all 4.5 g of hydrogen chloride and then 6.5 g of cyanic acid in gaseous form (in a stream of nitrogen) are introduced. The introduction is carried out for a period of 5 hours and is in several portions. The whole is subsequently allowed to react for 1 hour, and the product is filtered off and washed with 1,2-dichloroethane and then with water.

After drying at 60° C. in vacuo, 16.0 g of carbamazepine are obtained.

A batch treated in a similar manner was concentrated by evaporation when the reaction was complete and the residue was digested cold with toluene and filtered off. After washing with toluene and water and drying in vacuo at 60° C., 22.5 g of carbamazepine were obtained.

p EXAMPLE 7

29.0 g of iminostilbene are suspended in 150 ml of ethyl acetate at 20° C. First of all 0.6 g of hydrogen chloride and then 9.7 g of cyanic acid in gaseous form (in a stream of nitrogen) are introduced.

After stirring for 15 hours at 20° C., the product is filtered off, washed with ethyl acetate and then dried in vacuo at 60° C. 32.0 g of carbamazepine are obtained.

An analogous test at 50° C. reaction temperature yielded 29.4 g of carbamazepine.

EXAMPLE 8

19.3 g of iminostilbene are suspended in 200 ml of ethyl acetate and 1.0 ml of sulphuric acid (98 %) is added.

At 25° C., 6.5 g of monomeric cyanic acid (in a stream of nitrogen) are introduced. The whole is left to stand overnight, then concentrated to dryness by evaporation in vacuo, and the residue is taken up with toluene. After filtration, washing with toluene and water and drying at 80° C. in vacuo, 19.7 g of carbamazepine are obtained.

EXAMPLE 9

19.3 g of iminostilbene are heated to 45° C. with 100 ml of acetic acid. In the course of 1½ hours, 6.5 g of monomeric cyanic acid (in a stream of nitrogen) are introduced and the whole is left to react for 12 hours at 40° C. After cooling to 15° C., filtration is carried out followd by washing cold with acetic acid and drying in vacuo at 60° C.

The resulting crude product is recrystallised from methanol/water (7:3) and yields 19.1 g of carbamazepine.

EXAMPLE 10

29.0 g of iminostilbene are heated to 45° C. in 150 ml of acetic acid. In the course of 1½ hours, 9.7 g of monomeric cyanic acid (in a stream of nitrogen) are introduced and the whole is then allowed to react for 2 hours at 40° C. and for 12 hours at 20° C.

After the addition of 15 ml of water, the whole is cooled to 0° C. and, after 1 hour, the product is filtered off and washed twice with 15 ml of acetic acid and water to give a crude product which, after recrystallisation from methanol/water (7:3), yields 29.1 g of carbamazepine.

We claim:

1. A process for the manufacture of carbamazepine comprising reacting iminostilbene
   (a) in an aliphatic carboxylic acid; an aliphatic carboxylic acid in the presence of a mineral acid; or an aliphatic ester of an aliphatic carboxylic acid, an aromatic or araliphatic hydrocarbon or a haloaliphatic solvent in the presence of a mineral acid with cyanic acid; or
   (b) in an aliphatic carboxylic acid, and aliphatic ester of an aliphatic carboxylic acid, an aromatic or araliphatic hydrocarbon or a halo-aliphatic solvent with a salt of cyanic acid and an excess of a mineral acid.

2. A process according to claim 1 wherein the mineral acid is hydrochloric acid or sulfuric acid.

3. A process according to claim 1 wherein the reaction with cyanic acid is in acetic acid which thereby is both the acidic agent and the solvent.

4. A process according to claim 1, characterised in that the solvent used is toluene, xylene, 1,2-dichloroethane, acetic acid or ethyl acetate.

5. A process according to claim 1 wherein the reaction is carried out in a temperature range of from approximately 0° C. to approximately 120° C.

6. A process according to claim 1 wherein a small excess of hydrogen chloride is introduced into a suspension of sodium cyanate in ethyl acetate and then an amount of iminostilbene at most equimolar to the amount of sodium cyanate used is added.

7. A process according to claim 1, wherein an approximately 2% to approximately 10% excess of hydrogen chloride is introduced into a suspension of sodium isocyanate in ethyl acetate, and then from approximately 0.6 to approximately 0.9 times the molar amount of the N,N-(dibenzohexatrienylene)amine relative to the amount of sodium cyanate used is added, and the whole is heated to from approximately 40° C. to approximately 70° C.

8. A process according to claim 1 wherein from approximately +10° C. to approximately +120° C., an approximately 5% to approximately 40% molar excess of sulphuric acid is added to a suspension of aminostilbene in acetic acid and then an amount of sodium isocyanate that is at least equimolar to the amount of iminostilbene used is added.

9. A process according to claim 1, wherein an approximately 5% to approximately 40% excess of sulphuric acid is added to a suspension of the N,N-(dibenzohexatrienylene)amine in acetic acid and then from approximately 1.25 mols to approximately 1.75 mols of sodium isocyanate are added per mol of the amine.

10. A process according to claim 1, wherein an approximately 25% to approximately 75% excess of cyanic acid is introduced into a suspension of the N,N-(dibenzohexatrienylene)amine in acetic acid.

11. A process according to claim 1, wherein first from approximately 1 to approximately 15 mol % of hydrogen chloride and then an approximately 25% to approximately 75% excess of cyanic acid are introduced into a suspension of the N,N-(dibenzohexatrienylene)amine in toluene, xylene, 1,2-dichloroethane or ethyl acetate.

12. A process according to claim 1, wherein an approximately 25% approximately 75% excess of cyanic acid is introduced into a suspension of a mixture of from approximately 0.8 to approximately 0.96 molar proportions of the N,N-(dibenzohexatrienylene)amine and from approximately 0.04 to approximately 0.2 molar proportions of iminostilbene hydrochloride, wherein the total of molar proportions is equal to one.

* * * * *